US00RE47590E

(19) United States
(12) Reissued Patent
Hayes-Pankhurst et al.

(10) Patent Number: US RE47,590 E
(45) Date of Reissued Patent: *Sep. 3, 2019

(54) PUMP WITH CONVEYING CHAMBER FORMED IN OUTER ROTOR SURFACE

(71) Applicant: QUANTEX PATENTS LIMITED, London (GB)

(72) Inventors: Richard P. Hayes-Pankhurst, London (GB); Graham K. Lacy, London (GB); Christopher E. Nightingale, London (GB)

(73) Assignee: QUANTEX PATENTS LIMITED, London (GB)

( * ) Notice: This patent is subject to a terminal disclaimer.

(21) Appl. No.: 14/252,409

(22) Filed: Apr. 14, 2014

Related U.S. Patent Documents

Reissue of:
(64) Patent No.: 7,674,100
Issued: Mar. 9, 2010
Appl. No.: 11/069,043
Filed: Mar. 2, 2005

U.S. Applications:
(63) Continuation of application No. 13/449,985, filed on Apr. 18, 2012, now Pat. No. Re. 44,841, which is an application for the reissue of Pat. No. 7,674,100.

(30) Foreign Application Priority Data

Sep. 7, 2004 (GB) ..... 0419848.7

(51) Int. Cl.
*B23P 19/04* (2006.01)
*F04C 14/26* (2006.01)
(Continued)

(52) U.S. Cl.
CPC ..... *F04C 14/26* (2013.01); *A61M 5/14232* (2013.01); *A61M 5/14236* (2013.01);
(Continued)

(58) Field of Classification Search
CPC .. F04C 5/00; F04C 19/00; F04C 14/26; F04C 15/0015; F04C 13/00; F04C 11/001;
(Continued)

(56) References Cited

U.S. PATENT DOCUMENTS 1,983,033 A * 12/1934 Hutchison, Jr. ..... 418/153
2,840,991 A * 7/1958 Nisbet ..... 60/447
(Continued)

FOREIGN PATENT DOCUMENTS

DE 19916252 A1 * 11/2000
EP 0799996 A2 * 10/1997
(Continued)

OTHER PUBLICATIONS

Merriam-Webster's Collegiate Dictionary, 10th ed., 1998, p. 996.*

*Primary Examiner* — Jeffrey L Gellner

(57) ABSTRACT

A pump is formed by a housing (10) having an inlet (11) for connection to a source of fluid and an outlet (12) for pumped fluid. A rotor (15) is rotatable within the housing and the inlet (11) and the outlet (12) are spaced apart around the path of the rotor (15) in the housing. The rotor (15) has surfaces (16a, 16b, 16c, 16d) that form, with the housing (10), closed chambers (18a, 18b, 18c, 18d) which travel around the housing (10) to convey fluid from the inlet (11) to the outlet (12). The housing (10) carries a seal (14) that is located between the inlet (11) and the outlet (12) in the direction of travel of the rotor (15). The seal (14) co-operates with the rotor surfaces (16a, 16b, 16c, 16d) as the surfaces (16a, 16b, 16c, 16d) pass between the outlet (12) and the inlet (11) to prevent the formation of a chamber during said passage and so prevent fluid flow from the outlet (12) to the inlet (11). Such a pump is easily and cheaply produced and is particularly useful in medical applications.

20 Claims, 8 Drawing Sheets

(51) Int. Cl.

| | |
|---|---|
| ***B67D 1/10*** | (2006.01) |
| ***A61M 5/142*** | (2006.01) |
| ***F04C 15/00*** | (2006.01) |
| ***F04C 13/00*** | (2006.01) |
| ***F04C 5/00*** | (2006.01) |
| ***F04C 2/356*** | (2006.01) |
| ***F04C 11/00*** | (2006.01) |
| *F04C 2/22* | (2006.01) |

(52) U.S. Cl.
CPC ..... *B67D 1/10* (2013.01); *F04C 2/3566* (2013.01); *F04C 5/00* (2013.01); *F04C 11/001* (2013.01); *F04C 13/00* (2013.01); *F04C 15/0015* (2013.01); *F04C 2/22* (2013.01)

(58) Field of Classification Search
CPC ..... F04C 2/3566; F04C 2/22; A61M 5/1432; A61M 5/14236; B67D 1/10
See application file for complete search history.

(56) References Cited

U.S. PATENT DOCUMENTS

| | | | | | |
|---|---|---|---|---|---|
| 2,845,872 | A | * | 8/1958 | Farron et al. | 418/150 |
| 3,059,583 | A | * | 10/1962 | Huber | 417/410.3 |
| 3,282,496 | A | | 11/1966 | Radziwill | |
| 3,375,789 | A | * | 4/1968 | Easton | 415/199.3 |
| 3,642,390 | A | * | 2/1972 | Ostberg | 418/156 |
| 3,771,901 | A | * | 11/1973 | Svensson | 418/156 |
| 3,829,259 | A | * | 8/1974 | Baynes | 418/121 |
| 4,017,208 | A | * | 4/1977 | Vonnegut | 415/90 |
| 4,028,021 | A | * | 6/1977 | Berkowitz | 418/153 |
| 4,390,328 | A | * | 6/1983 | Fickelscher | 418/45 |
| 6,022,201 | A | * | 2/2000 | Kasmer | F04C 2/3441 418/1 |
| 6,095,783 | A | * | 8/2000 | Hansen et al. | 418/61.1 |
| 2002/0059913 | A1 | * | 5/2002 | Barrett | 123/205 |
| 2006/0228245 | A1 | * | 10/2006 | Adahan | 418/125 |

FOREIGN PATENT DOCUMENTS

| | | | | |
|---|---|---|---|---|
| GB | 482750 | A | | 4/1938 |
| GB | 1109374 | A | | 4/1968 |
| JP | 58187595 | A | | 11/1983 |
| JP | 60111078 | A | | 6/1985 |
| JP | 60240890 | A | * | 11/1985 |

* cited by examiner

PUMP WITH CONVEYING CHAMBER FORMED IN OUTER ROTOR SURFACE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS REFERENCE TO RELATED APPLICATIONS*

*Notice: More than one reissue application has been filed for the reissue of U.S. Pat. No. 7,674,100. The reissue applications are the present application (Ser. No. 14/252,409) and reissue application Ser. No. 13/449,985. The present application is a continuation reissue of application Ser. No. 13/449,985 and a reissue application of U.S. Pat. No. 7,674,100, now U.S. Pat. No. Re 44,841, which claims the benefit of the filing date of GB 0419848.7 filed Sep. 7, 2004.*

BACKGROUND TO THE INVENTION

1. Field of the Invention

The invention relates to pumps.

2. Background to the Invention

A known form of pump comprises a housing with an inlet for connection to a source of fluid and an outlet for pumped fluid with the inlet and the outlet being spaced apart around a path of a rotor within the housing. The rotor includes at least one surface forming, with the housing, a closed chamber travelling around the housing to convey fluid around the housing.

In such pumps, a problem is the prevention of direct communication between the outlet and inlet. In JP-A-60240890, a flexible film is fixed to a partition wall between the outlet and the inlet and engages partitioning pieces on the rotor. In GB-A-482750, the rotor carries sections that seal against an arcuate surface of the housing. In U.S. Pat. No. 3,282,496 slidable elements are forced by pressure against the chamber-forming surfaces of the rotor. In JP-A-60111078, the rotor carries movable seals formed by various deformable bodies that seal against the housing between the outlet and the inlet. In GB-A-1109374, the rotor carries seals that seal against the housing between the inlet and the outlet

SUMMARY OF THE INVENTION

According to the invention, there is provided pump comprising a housing, a rotor path defined within the housing, an inlet formed in the housing at a first position on said rotor path, an outlet formed in the housing at a second position on said rotor path spaced from said first position, a rotor rotatable in said housing, at least two apices formed on the rotor and sealing against said rotor path, at least one surface formed on said rotor between said at least two apices, a chamber formed by said at least one rotor surface between the at least two apices and the housing and travelling around said rotor path on rotation of the rotor to convey fluid around the housing, a resilient seal carried by the housing located on said rotor path and extending between the outlet and the inlet in the direction of rotation of said rotor that each apex seals with, and resiliently deforms, the seal, as each apex passes between the outlet and the inlet to prevent fluid flow from said outlet to said inlet past the seal.

The following is a more detailed description of some embodiments of the invention, by way of example, reference being made to the accompanying drawings in which:—

DESCRIPTION OF THE PREFERRED EMBODIMENTS

Figure 1:
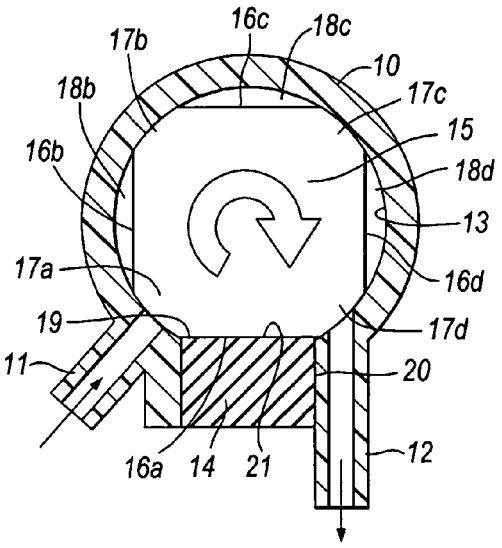
FIG. 1 is a schematic cross-section through a pump including a housing provided with an inlet and outlet and a rotor rotatable within the housing and sealing against a seal provided by the housing, the rotor being shown in a first angular position.
Figure 2:
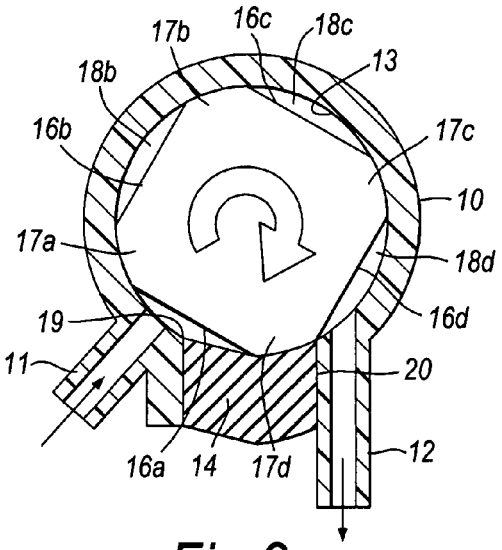
FIG. 2 is a similar view to FIG. 1 but showing the rotor rotated by about 30° from the position shown in FIG. 1.
Figure 3:
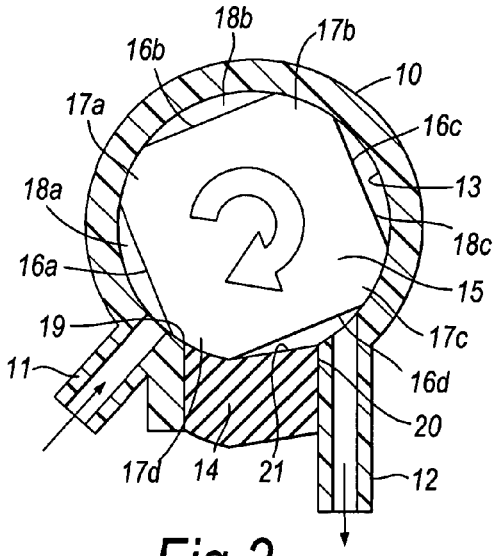
FIG. 3 is a similar view to FIG. 1 but showing the rotor rotated by about 60° from the position shown in FIG. 1.

Referring first to FIGS. 1 to 3, the pump is formed by a housing indicated generally at 10 which may be formed by a plastics moulding of, for example, polyethylene or polypropylene. The housing 10 is formed with an inlet 11 for connection to a source of fluid and an outlet 12 for pumped fluid. The interior of the housing 10 is cylindrical. The portion of the interior of the housing 10 between the outlet 12 and the inlet 11, again in clockwise direction as viewed in FIGS. 1 to 3, carries a seal 14 that will be described in more detail below.

The housing 10 contains a rotor 15. The rotor 15 may be formed of stainless steel or as a precision injection moulded plastics part formed from a resin such as acetal. As seen in the Figures, the rotor 15 is generally of circular cross-section and includes four recessed surfaces 16a, 16b, 16c and 16d of equal length equiangularly spaced around the rotor and interconnected by apices 17a, 17b, 17c and 17d formed by unrelieved portions of the rotor 15. Accordingly, each apex is rounded with a curvature that matches the curvature of the cylindrical housing surface 13 so that the rotor 15 is an interference fit within the cylindrical housing surface 13. As a result, each recessed surface 16a, 16b, 16c and 16d forms a respective chamber 18a, 18b, 18c and 18d with the cylindrical housing surface 13 as each surface 16a, 16b, 16c, 16d travels around that housing surface 13. If the housing 10 is formed from a resilient plastics material that deforms under load, the rotor 15 may be arranged to distend slightly the housing 10, so ensuring a fluid-tight seal around each surface 16a, 16b. 16c. 16d.

The rotor 15 is rotated in a clockwise direction in FIGS. 1 to 3 by a drive (not shown in the Figures).

The seal 14 is formed by a block of elastomeric material that is compliant, flexible and resilient such as that sold under the trade mark Hytrel. The seal 14 is connected to the housing 10 to prevent fluid passing between the seal 14 and the housing 10. This may be by use of an adhesive. Alternatively, the seal 14 could be moulded with the housing 10 in a 2-shot injection moulding process *or an insert molding process, or an over-molding process, or a dual shot molding process*. In this latter case, the material of the seal 14 must be such that it welds to the housing to prevent leakage. The seal 14 has a first axial edge 19 adjacent the inlet 11 and a second axial edge 20 adjacent the outlet 12. The seal 14 has a rotor engaging surface 21 that has a length between the first and second edges 19, 20 that is generally equal to the length of each of the recessed surfaces 16a, 16b, 16c and 16d between the associated apices 17a, 17b, 17c, 17d and is shaped to match the shape of each recessed surface 16a, 16b, 16c, 16d. The axial extent of the seal 14 is that at least the same as the axial extent of the recessed surfaces 16a, 16b, 16c, 16d. The seal 14 projects into the space defined by an imaginary cylinder described by a continuation of the cylindrical surface 13 between the inlet 11 and the outlet 12. The seal 14 may be flexed between the first and second axial edges 19, 20 so that it bows outwardly relatively to the seal 14 towards the axis of the rotor 15 where the recessed surfaces 16a, 16b, 16c, 16d are concave.

The natural resilience of the material will tend to return the seal 14 to the undistorted disposition after distortion by the rotor 15 and this may be assisted by a spring (not shown) acting on the radially outer end of the seal 14.

The operation of the pump described above with reference to FIGS. 1 to 3 will now be described. The inlet 11 is connected to a source of fluid to be pumped and the outlet 12 is connected to a destination for the pumped fluid. The rotor 15 is rotated in a clockwise direction as viewed in FIGS. 1 to 3. In the position shown in FIG. 1, the rotor surface 16a engages resiliently the seal surface 21. In this way, the space between the housing 10 and the rotor 15 is closed in this zone and the passage of fluid from the outlet 12 to the inlet 11 is prevented. In this position, the apex 17a is aligned with the inlet 11 while the rotor surfaces 16b, 16c, 16d form respective sealed chambers 18b, 18c, 18d with the cylindrical housing surface 13. As a result of earlier revolutions of the rotor 15, these chambers 18b, 18c and 18d are filled with fluid in a manner to be described below.

Referring next to FIG. 2, on rotation of the rotor 15 by about 30°, the chamber 18d is now connected to the outlet 12. The associated apex 17d contacts the seal surface 21 and seals against that surface. Accordingly, the rotating rotor 15 forces fluid from the chamber 18d out of the outlet 12. In addition, the apex 17a previously aligned with the inlet 11, moves away from the inlet 11 and allows the rotor surface 16a to separate from the sealed surface 21 to begin to form a chamber 18a (FIG. 3) with the cylindrical housing surface 13 and with the apex 17d against the seal surface 21.

Referring next to FIG. 3, a further rotation of the rotor 15 by about 60° from the position shown in FIG. 1, results in the rotor surface 16d that previously formed the chamber 18d adjacent with outlet 12 begins to contact the seal surface 21 and sealing against that surface 21. Thus, the chamber 18d reduces in volume until it no longer exists and fluid from that chamber is forced through the outlet 12. At the same time, the rotor surface 16a formerly in contact with the seal surface 21 is now clear of that surface 21 and forms a chamber 18a with the cylindrical housing surface 13 and the chamber 18a receives fluid from the inlet 11. The apex 17d between the surfaces 16a and 16d moves out of engagement with the seal surface 21 and starts to align with the inlet 11.

The rotor 15 then moves to a position equivalent to the position shown in FIG. 1 and pumping continues. In this way, fluid is pumped between the inlet 11 and the outlet 12.

It will be appreciated that the rate of flow of liquid is proportional to the rate of rotation of the rotor 15 and the volumes of the chambers 18a, 18b, 18c and 18d. Although the rotor 15 is shown as having four surfaces 16a, 16b, 16c, 16d, it could have any number of surfaces such as one or two or three surfaces or more than four surfaces. The surfaces 16a, 16b, 16c, 16d may be planar, or may be, for example, convexly or concavely curved. Preferably they are shaped as indentations formed by the intersection with the rotor 15 of an imaginary cylinder having its axis at 90° to the axis of the rotor and offset to one side of the rotor axis. As described above, the rotor engaging surface 21 of the seal 14 may be shaped to compliment the shape of the surfaces 16a, 16b, 16c, 16d.

At all times, the seal 14 acts to prevent the formation of a chamber between the outlet 12 and the inlet 11 in the direction of the rotor 15. The resilience of the seal 14 allows it always to fill the space between the inlet 11 and the outlet 12 and the portion of the rotor 15 in this region. As the pressure differential between the inlet 11 or the outlet 12 increases, there is an increased tendency for fluid to pass between the seal 14 and the rotor 15. The use of a spring acting on the seal 14, as described above, will decrease that tendency and so allow the pump to operate at higher pressures. Thus, the force applied by the spring determines the maximum pump pressure. Pumps are known in which the outlet and the inlet are separated by a thin vane extending from the housing and contacting the rotor. In such pumps, there is a volume of fluid between the outlet and the inlet and a large pressure gradient across the vane that will increase as the speed of rotation of the rotor. As a result, there is an increased liability to leakage across the vane. In the pump described above with reference to the drawings, although there is a pressure differential between the inlet and the outlet, there is a much more gradual gradient as the fluid is gradually squeezed out of the chambers 18a, 18b, 18c and 18d into the outlet 12 and then, after further rotation of the rotor 15, gradually introduced into a chamber 18a, 18b, 18c and 18d on the inlet side. This reduces the possibility of leakage and allows the pump to provide an accurate metered flow. The seal 14 acts as a displacer displacing the fluid between the inlet 11 and the outlet 12.

Figure 4:
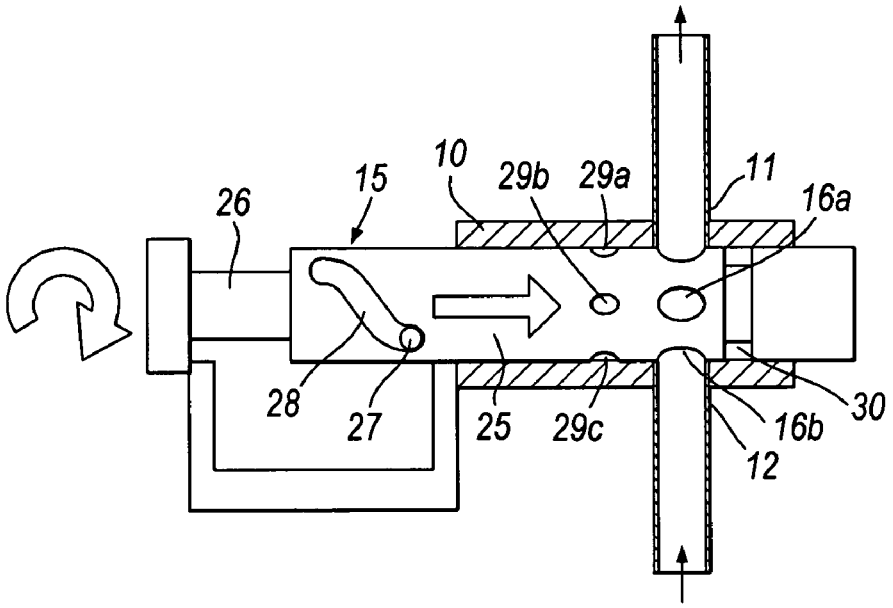
FIG. 4 is a schematic side elevation partly in section of a first form of pump incorporating a housing and a rotor of the kind shown in FIGS. 1 to 3 with the rotor in a first axial position.
Figure 5:
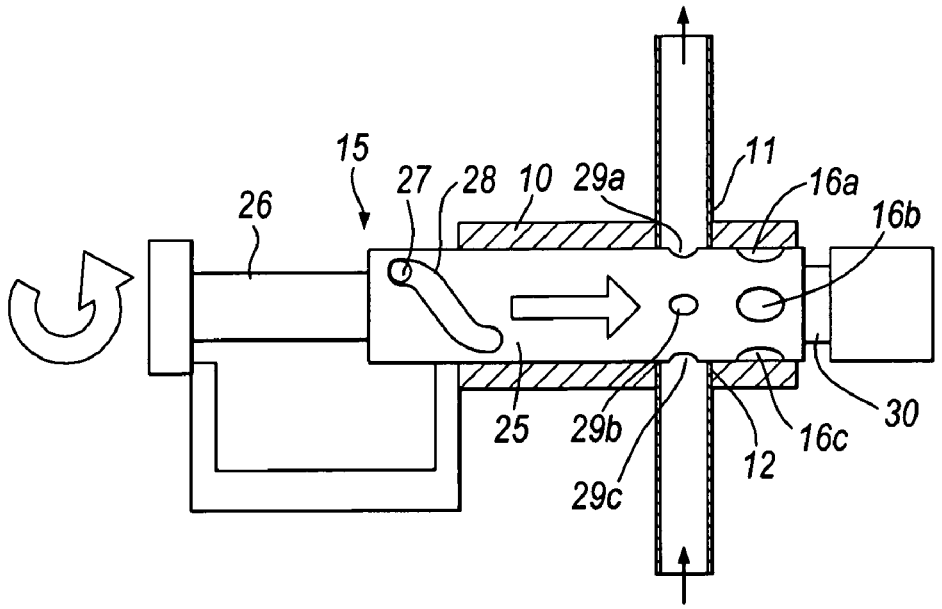
FIG. 5 is a partial view of the pump of FIG. 4 showing the rotor in a second axial position.

Referring next to FIG. 4, this Figure shows a pump operating on the principles described above with reference to FIGS. 1 to 3. Parts common to FIGS. 1 to 3 and to FIG. 4 are given the same reference numerals and will not be described in detail.

In this embodiment, the rotor 15 is formed in two parts; an outer cylindrical sleeve 25 and an inner rod 26. The rod 26 is provided with a radially extending pin 27 that engages a helical slot 28 provided in the sleeve 25.

The sleeve 25 is provided with a first set of surfaces 16a, 16b, 16c, 16d as described above with reference to FIGS. 1 to 3 co-operating with the housing 10 having an inlet 11 and an outlet 12 as also described above with reference to FIGS. 1 to 4.

In addition, however, the sleeve 25 is also provided with a second set of recessed surfaces 29a, 29b, 29c, 29d at a position on the sleeve 25 axially spaced relative to the first mentioned surfaces 16a, 16b, 16c, 16d. These second surfaces 29a, 29b, 29c, 29d have a smaller circumferential extent than the first-mentioned surfaces 16a, 16b, 16c, 16d. In addition, the sleeve 25 is also formed with a circumferential groove 30 spaced axially from the first mentioned surfaces 16a, 16b, 16c, 16d and the other side of the surfaces 16a, 16b, 16c, 16d from the second surfaces 29a, 29b, 29c, 29d.

In use, rotation of the rotor 15 in a direction shown in FIG. 4 causes the pump to operate as described above with reference to FIGS. 1 to 3. However, if the rotor drive is reversed, with the rod 26 held in a fixed axial position relative to the housing 10, the pin 27 will travel along the slot 28 and move the sleeve 25 axially relative to the rod 26 to a position in which the second surfaces 29a, 29b, 29c, 29d are aligned with the inlet 11 and the outlet 12. Reverse rotation of the rod 26 will then cause the second surfaces 29a, 29b, 29c, 29d to pump fluid as described above with reference to FIGS. 1 to 3. In this case, however, since the second surfaces 29a, 29b, 29c, 29d have a smaller angular extent, the pump volume will be smaller so allowing lower flow rates.

It will be appreciated that, since the pump is symmetrical about a plane including the rotor axis and midway between the inlet 11 and the outlet 12, the pump would operate on reverse rotation of the rotor 15 to draw fluid from the outlet 12 and deliver it to the inlet 11. It will also be appreciated that the surfaces 16a, 16b, 16c and 16d will need to have a curvature that is similar to a corresponding portion of the curvature on the seal 14 however because the surfaces are smaller the seal with have a permanently bowed disposition.

Figure 6:
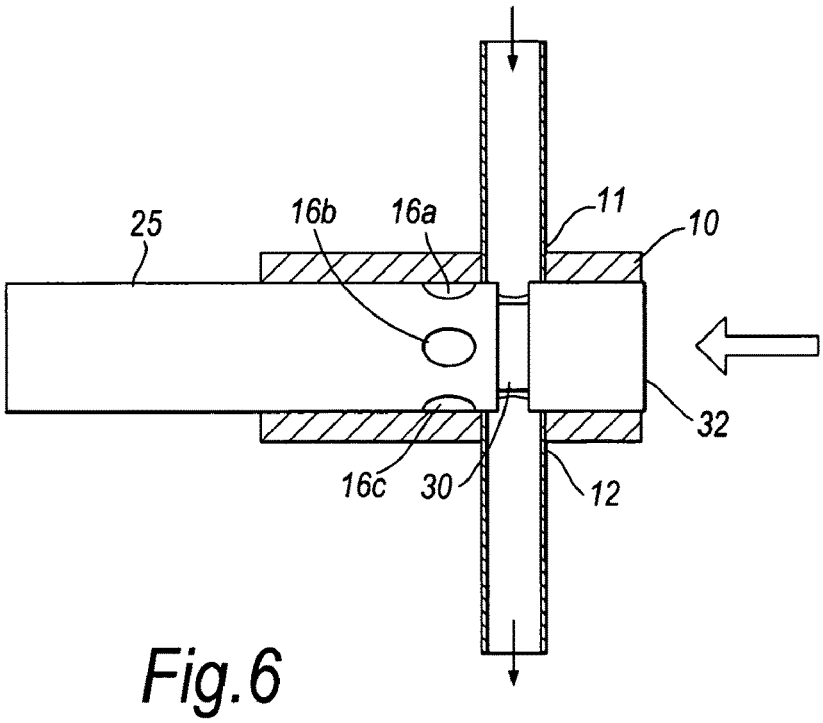
FIG. 6 is a similar view to FIG. 4 omitting parts of the rotor and housing and showing the rotor of the pump of FIG. 4 in a third axial position

The end 32 of the sleeve 25 remote from the rotor drive projects from the housing 10. It is possible manually to push this end 32 so moving the sleeve 25 into the housing 10 until a groove 30 is aligned with the inlet 11 and the outlet 12. When in this position, as shown in FIG. 6, direct communication is permitted between the inlet 11 and the outlet 12.

Figure 7:
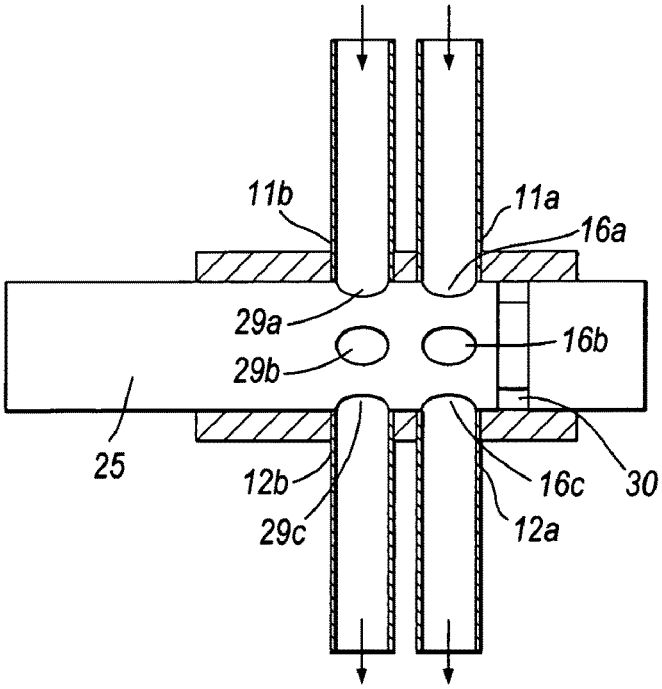
FIG. 7 is a similar view to FIG. 6 but showing an alternative embodiment of the housing and the rotor.

An alternative proposal is shown in FIG. 7 in which the housing 10 includes two inlets 11a and 11b and two outlets 12a and 12b. The first mentioned rotor surfaces 16a, 16b, 16c, 16d are aligned with the first inlet 11a and the first outlet 12a and the second rotor surfaces 29a, 29b, 29c, 29d are aligned with the second inlet 11b and the second outlet 12b. In this way, as the rotor rotates, additional volume is pumped so increasing the flow rate. As seen in FIG. 7, in this case, the second surfaces 29a, 29b, 29c, 29d are sized similarly to the first surfaces 16a, 16b, 16c, 16d. Of course, the second surfaces 29a, 29b, 29c, 29d need not be sized similarly to the first surfaces 16a, 16b, 16c, 16d; they could have any relative size. It will be appreciated that by displacing the rotor 15 axially relative to the housing 10, the first-mentioned rotor surfaces 16a, 16b, 16c and 16d could be aligned with the second inlet 11b and the second outlet 12b with the second rotor surfaces 29a, 29b, 29c and 29d being inoperative and covered by the housing 10 and the first inlet 11a and the first outlet 12a being [closed] *in direct communication via aligned groove 30*. Alternatively, the rotor 15 could be displaced in the opposite direction relative to the housing so that the second rotor surfaces 29a, 29b, 29c and 29d are aligned with the first inlet 11a and the first outlet 12a with the first-mentioned rotor surfaces 29a, 29b, 29c and 29d being inoperative and covered by the housing 10 and the second inlet 11b and the second outlet 12b being closed.

Figure 8:
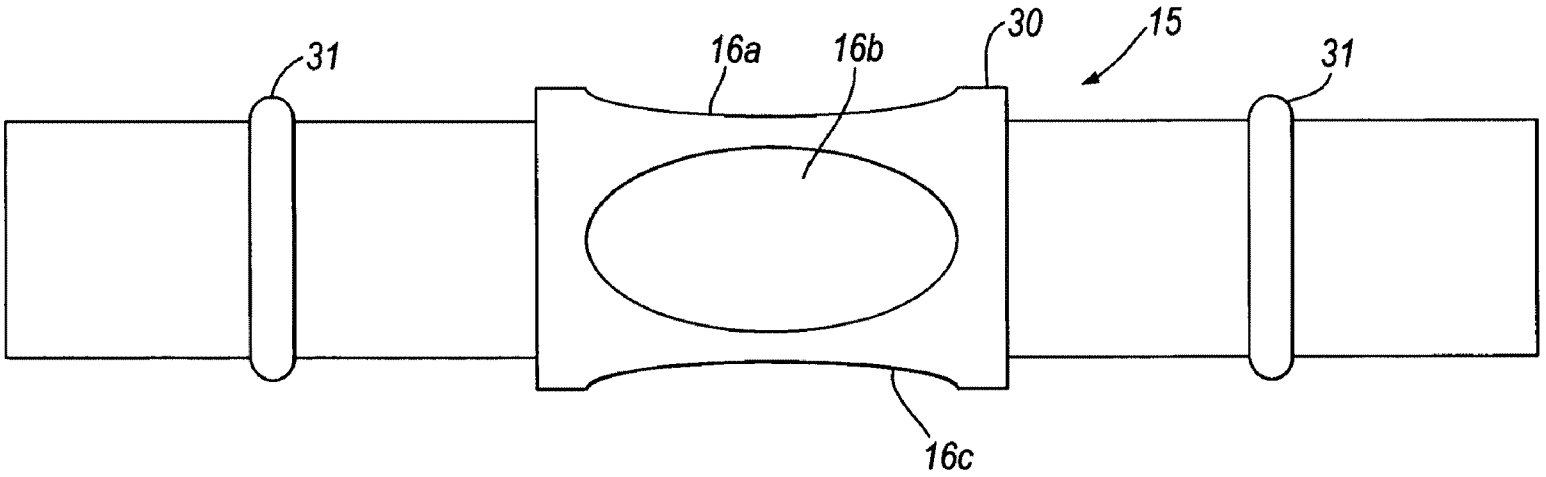
FIG. 8 is a side elevation of a further embodiment of the rotor.

In the embodiments described above with reference to the drawings the rotor 15 is shown as a solid cylinder with the recessed surfaces 16a, 16b, 16c and 16d formed in that surface. This need not be so. As shown in FIG. 8, the rotor 15 may be formed with a central cylindrical land 30 in which the recessed surfaces 16a, 16b, 16c, 16d are formed with two annular ribs 31 arranged on respective opposite sides of the land 30. The land 30 and the ribs 31 seal against the housing 10 using the elasticity of the housing 10 to ensure fluid-tight seals. The radially relived areas between the ribs 31 and the land 30 reduce the frictional forces.

In FIGS. 1 to 3, the inlet 11 and the outlet 12 are shown at opposite axial ends of the seal 14. As an alternative, the inlet 11 or the outlet could be formed in the seal 14.

Figure 9:
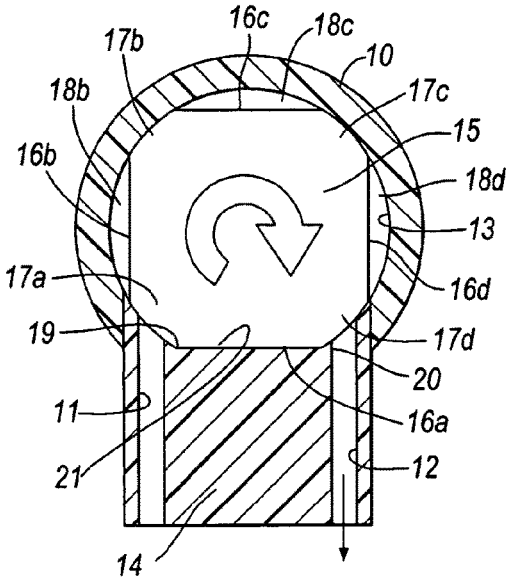
FIGS. 9 to 11 are similar views to FIGS. 1 to 3 but showing an alternative form of the housing.
Figure 10:
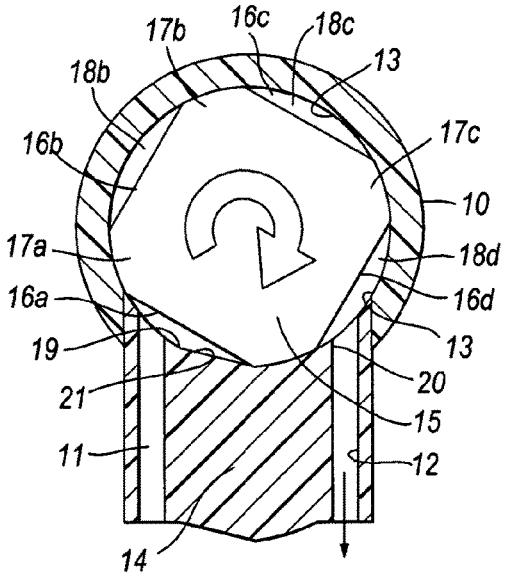
Figure 11:
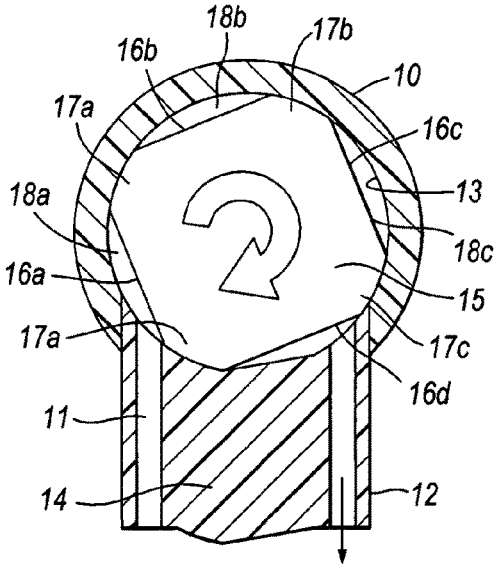

This is shown in FIGS. 9 to 11. The pump of FIGS. 9 to 11 has parts in common with the pump of FIGS. 1 to 3. These common parts will not be described in detail and will be given the same reference numerals in FIGS. 9 to 11 as in FIGS. 1 to 3. Referring to FIGS. 9 to 11, in this embodiment, the inlet 11 and the outlet 12 are formed in the seal 14. The angular spacing between the inlet 11 and the outlet 12 remains the same as in FIGS. 1 to 3, but the width of the seal 14 is increased. The pump of FIGS. 9 to 11 operates as described above with reference to FIGS. 1 to 3. However, the formation of the inlet 11 and the outlet 12 in the seal 14 has the advantage that the apices of the rotor 15 can remain in contact with the seal 14 before the outlet 12 and provide more precise delivery of the volume of fluid in the associated chamber 18a, 18b, 18c, 18d. Another advantage is the edge 20 of the outlet 12 is coincident with the end of the seal 14 which allows all the liquid to be expelled (scavenging) as the rotor surfaces 16a, 16b, 16c, 16d assume face to face contact with the seal 14.

The pumps described above with reference to the drawings can be used for pumping any fluid preferably containing no particulates. Such pumps may, however, find particular application in the pumping of medical fluids and may be used with intravenous administration sets. Such pumps allow aseptic pumping and metering of fluid to high volumetric accuracies. In this case, the inlet 11 and the outlet 12 may be connected in line before the housing 10 and the rotor 15 assembly are connected to a drive. The housing 10 and rotor assembly 15 may be supplied with the inlet 11 and the outlet 12 aligned with the groove 30 so that a delivery tube of the set is in a free flow condition and able to be primed as soon as the housing 10 and rotor 15 assembly is connected in-line. When the rotor 15 is connected to the drive, the making of the connection moves the rotor 15 to a position in which the rotor surfaces 16a, 16b, 16c, 16d are aligned with the inlet 11 and the outlet 12 so that the pump 10 is ready for metered operation. It is thus mechanically impossible for the rotor 15 to be in the free flow position when connected to the drive so that, should the drive fail, free flow is not possible.

Figure 12:
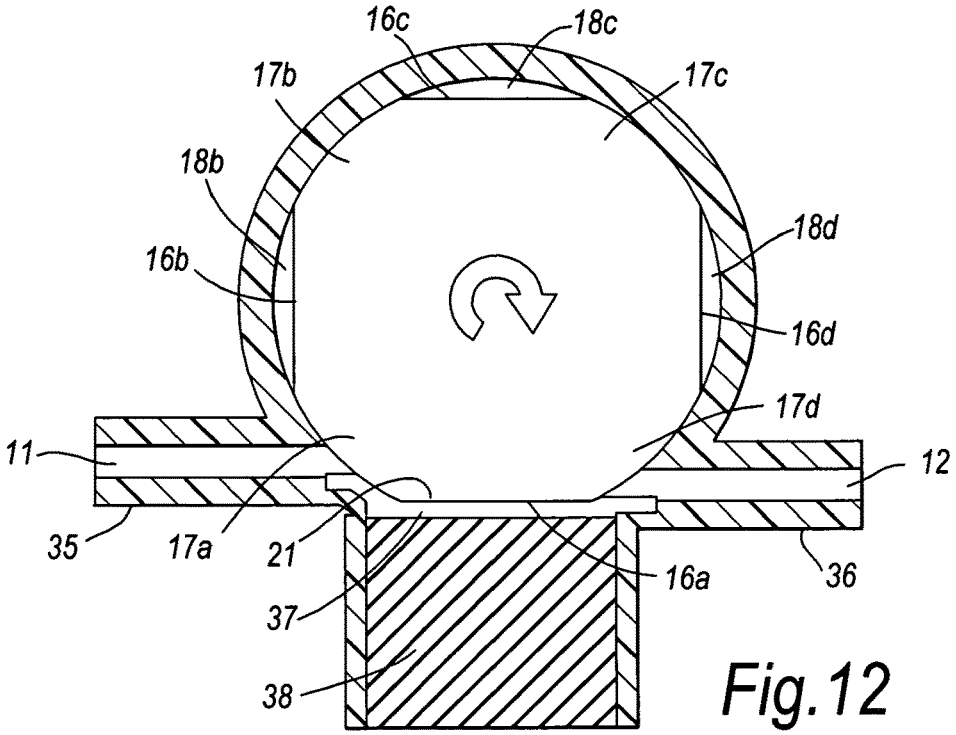
FIG. 12 is a similar view to FIG. 1 but showing a first modified form of the housing in which the inlet and the outlet are parallel but offset and in which the seal is formed by a resilient membrane.

Referring next to FIG. 12, parts common to FIGS. 1 to [111] *11* and to FIG. 12 will not be described in detail and will be given the same reference numerals. The housing 10 of FIG. 12 has the inlet 11 formed by a tube 35 extending in a direction generally tangential to the circular path described by the rotor 15. In addition, the outlet 12 is formed by a tube 36 also extending in a direction generally tangential to the circular path described by the rotor 15. The directions of the inlet tube 35 and the outlet tube 36 are thus parallel but, as seen in FIG. 12, are also offset. The effect of this is that the inlet 11 is spaced around the housing 10 from the outlet 12 by a distance such that the chamber 18a is fully exhausted through outlet 12 before the inlet 11 is open (so that the inlet 11 is closed by the apex 17a). This has the advantage of reducing the possibility of leakage between the outlet 12 and the inlet 11 and ensuring the chambers 18 are fully evacuated.

In the arrangement shown in FIG. 12, the outlet 12 is shown closer to the mid-point of the seal 13 that the inlet 11. This arrangement could be reversed with the inlet 11 being the nearer to the mid-way point of the seal 14.

Figure 13:
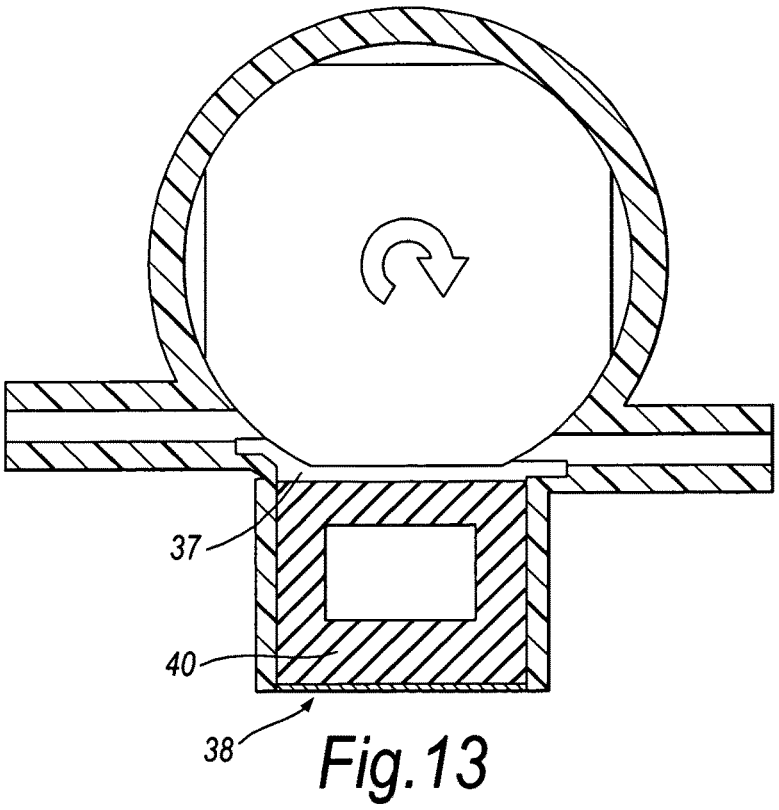
FIG. 13 is a view of the pump of FIG. 12 showing the membrane acted on by a pressurised fluid or gel.
Figure 14:
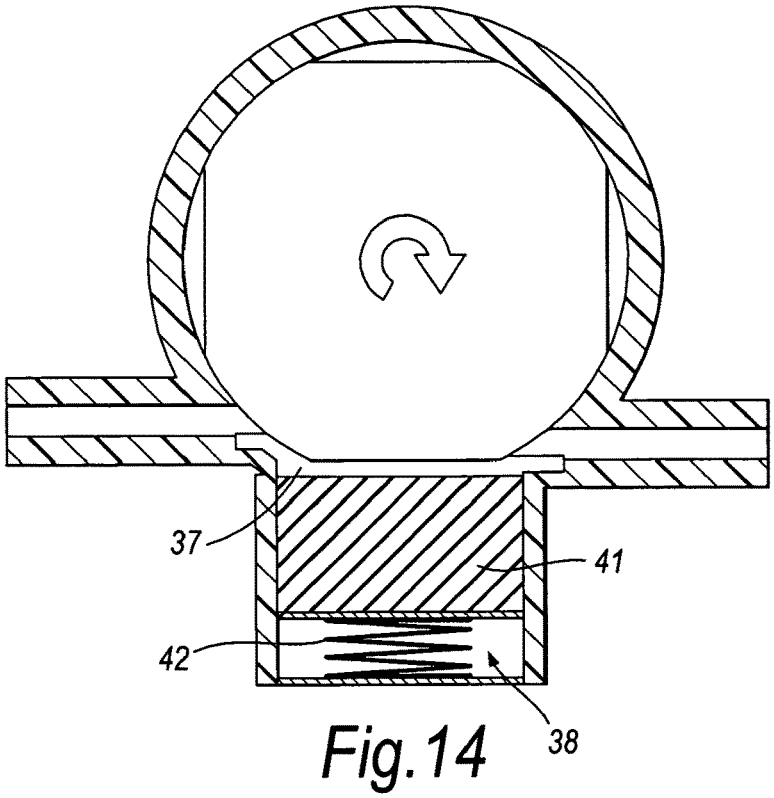
FIG. 14 is a view of the pump of FIG. 12 showing the membrane acted on by a spring.
Figure 15:
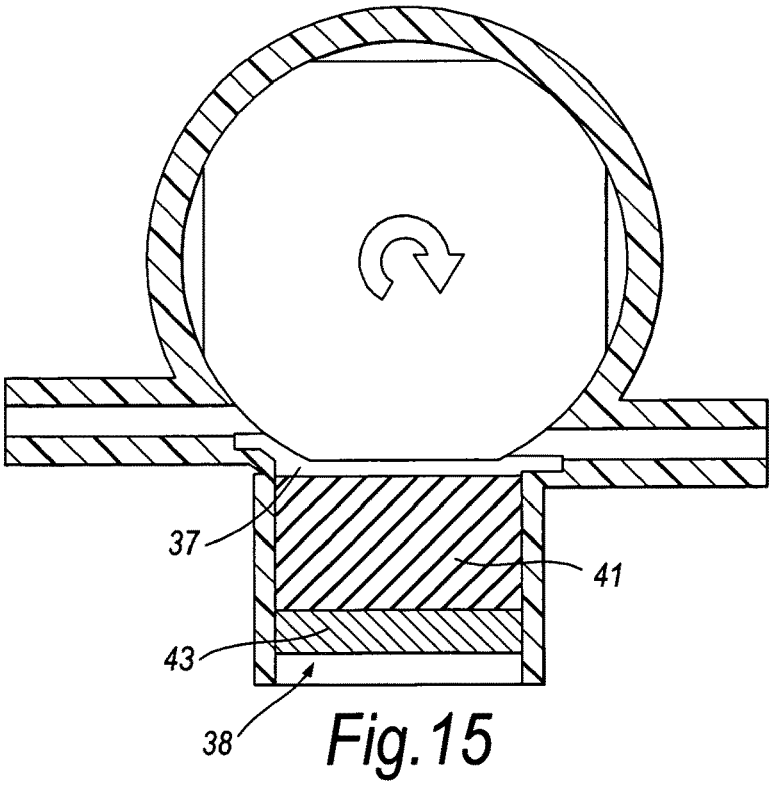
FIG. 15 is a view of the pump of FIG. 12 showing the membrane acted on by an adjustable screw.

In this embodiment, the seal 14 is formed by a membrane 37 that extends between the first and second axial edges 19, 20 of the housing 10 and between the outlet 12 and the inlet 11. The membrane 37 is supported by a member 38 that applies a resilient force to the membrane 37. This member 38 can have a number of forms. Some examples of this are shown in FIGS. 13, 14 and 15. Parts common to FIG. 12 and to FIGS. 13, 14 and 15 are given the same reference numeral and will not be described in detail. First, referring to FIG. 13 the member 38 could be formed by a resilient container 40 of gel or other fluid or gas that is held under pressure either by overfilling the container in manufacture. Secondly referring to FIG. 14, a movable cap 41 may bear against the membrane 27 under the action of a spring 42. Thirdly, referring to FIG. 15, the cap 41 may bear against the membrane 27 with a force determined by the adjustment of a screw 43.

The membrane 37 has a low coefficient of friction with the rotor 15 but is sufficiently stretched to prevent the formation of wrinkles when deformed outwardly by the apices 17. The membrane 37 seals closely against the rotor 15 to displace fluid in the chambers 18 and prevent leakage between the outlet 12 and the inlet 11.

The problem of communication between an outlet and an adjacent inlet is not confined to the case disclosed above where a single inlet and a single outlet are provided with fluid being conveyed between the single inlet and the single outlet. It is possible to have two or more inlets and two or more outlets spaced around the housing 10. In this case, the problem will still exist of preventing fluid communication between an outlet and a succeeding inlet, in the direction of rotation of the rotor, but the outlet and the inlet will not be associated with the same flow paths. An example of this will now be described with reference to FIG. 16.

Figure 16:
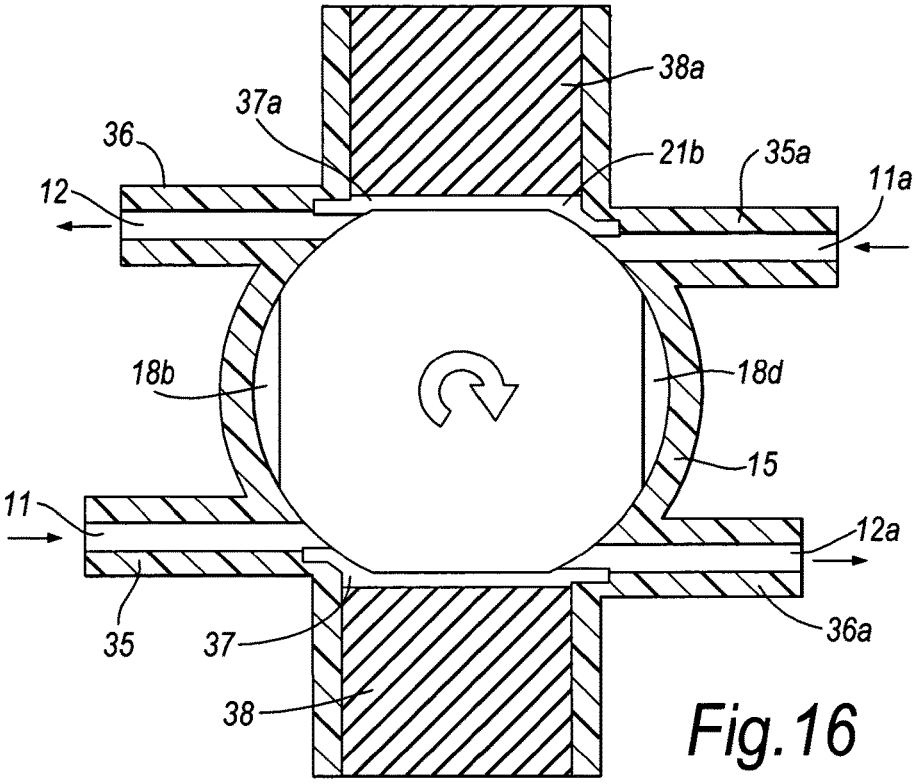
FIG. 16 is a similar view to FIG. 12 but showing a second modified form of the housing in which two inlets and two outlets are provided, with each inlet offset from the associated outlet, and with two resilient seals each formed by a respective resilient membrane.

Referring next to FIG. 16, parts common to FIG. 12 and to FIG. 16 will not be described in detail and will be given the same reference numerals. The housing 10 of FIG. 16 has, in comparison with the arrangement of FIG. 12, a second inlet 11a and a second outlet 11b. The second inlet 11a is formed by a second inlet tube 35a and the second outlet is formed by a second outlet tube 36a. The second inlet 11a is located on the housing 10 diametrically opposite the first inlet 11 and the first-mentioned and second inlet tubes 35, 35a are parallel. The second outlet 12a is located on the housing 10 diametrically opposite the first outlet 12 and the first mentioned and second outlet tubes 36, 36a are parallel. A second membrane 37a and resilient container 38a are provided, in any of the forms described above with reference to FIG. 12. The second membrane 37a is diametrically opposite the first-mentioned membrane 37.

In use, as the rotor 15 rotates, starting from the rotor position shown in FIG. 16, the apices 17a, 17b, 17c and 17d can cover the associated inlets and outlets 11, 12a, 11a and 12. Fluid in the chamber 18d passes to the second outlet 12a and fluid in the chamber 18b passes to the first outlet 12. The fourth apex 17d seals against the first membrane 37 and the second apex 17b seals against the second membrane 37a. The first chamber 18a then connects to the first inlet 11 while the third chamber 18b connects to the second inlet 11a. When the rotor 15 has rotated through 90° the configuration of the pump is again as shown in FIG. 16 and the above steps are repeated as rotation continues to pump fluid between the first inlet 11 and the first outlet 12 and between the second inlet 11a and the second outlet 12a.

It will be appreciated that, in this configuration, the seals formed by the membranes 37, 37a act to prevent fluid flow not between the inlet 11 and the associated outlet 12 and between the second inlet 11a and the associated second outlet 12a, but between the first outlet 12 and the second inlet 11a and between the second outlet 12a and the first inlet 11. The problem overcome is, however, the same as described above with reference to FIGS. 1 to 11 namely the prevention of fluid communication between an outlet and the seal succeeding inlet in the direction of rotation of the rotor.

It will be appreciated that the pump described above with reference to FIG. 16 could be used to pump two different fluids so that the two fluids will be accurately pumped at the same rate. Alternatively, the pump could be used to pump a single fluid at double the rate of the pump described above with reference to FIG. 12.

Figure 17:
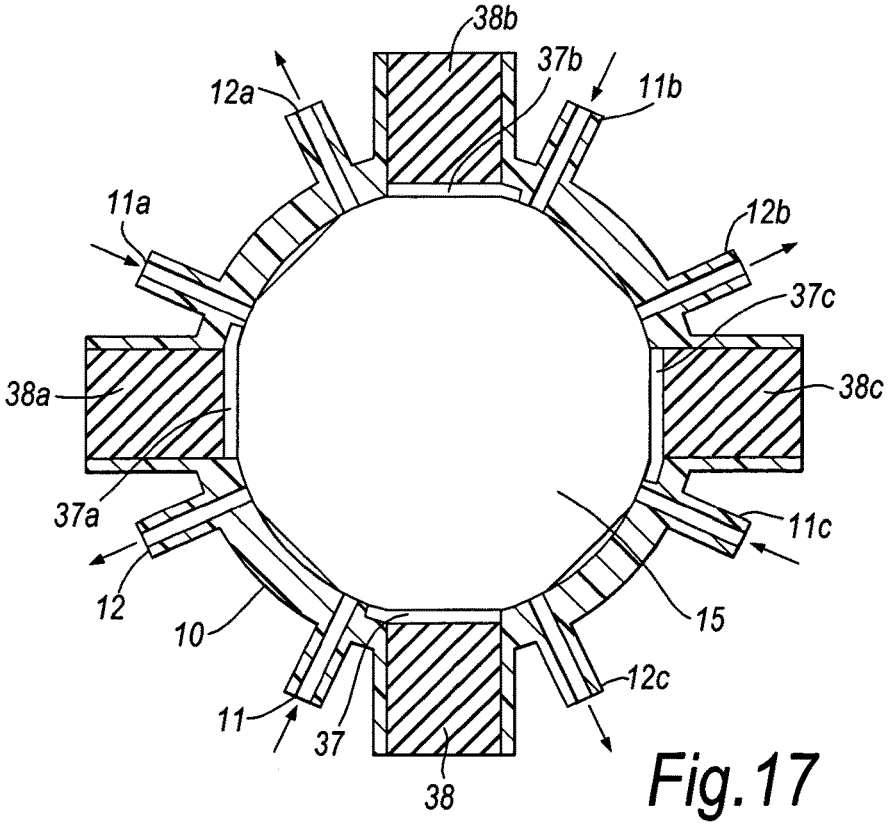
FIG. 17 is similar view to FIG. 16 but showing a third modified form of the housing in which four inlets and four outlets are provided, four seals are provided and the rotor forms eight chambers.

It will be appreciated that any of the pumps described above with reference to the drawings may have more or less than four chambers 18a, 18b, 18c, 18d. A single chamber is possible but will only give an output once per rotation of the rotor 15. A number of smaller chambers having a total volume of one large chamber may provide a smoother (less pulsed) output flow per revolution. In relation to the embodiment of FIG. 16, there may be more than two inlets and outlets where one or are a plurality of chambers is provided. The radial position and number of the inlets and outlets and seals can be chosen to be non-synchronous with the number of the chambers on the rotor (for example if there are 3 equi-spaced chambers on the rotor and 2 diametrically opposing inlets, outlets and seals) to provide a smoother flow. An example of such a pump is shown in FIG. 17 where parts common to FIG. 16 and to FIG. 17 are given the same reference numerals and are not described in detail. In the embodiment of FIG. 17, the rotor 15 forms eight chambers with the housing 10. Four pairs of inlets and outlets, 11, 11a, 11b, 11c and 12, 12a, 12b, 12c are provided. Foul seals are provided each formed with a respective membrane 37, 37a, 37b, 37c supported by a respective member 38, 38a, 38b, 38c. The members 38, 38a, 38b, 38c can have any of the forms described above with reference to FIGS. 13 to 15. As in FIG. 16, each membrane 37, 37a, 37b, 37c is located between an outlet 12c, 12, 12a, 12b of one pair and the inlet 11, 11a, 11b, 11c of the next succeeding pair of inlets and outlets. The pump of FIG. 17 operates as described above with reference to FIG. 16 but with the addition of two further pairs of inlets and outlets.

It will be appreciated, that the pumps described above with reference to the drawings are formed from few parts—effectively, the housing 10, a rotor 15 and a seal 14. It is possible to form the housing 10 and seal 14 in a two-shot injection moulding process. Alternatively all three elements can be produced in a single assembly injection moulding process in which the rotor 15 is moulded first with the housing 10 then being moulded around the rotor 15 and finally the seal 14 moulded into the housing. The use of such a moulding process allows a pump to be manufactured cheaply and simply to an extent that may allow the pump to be used as a disposable pump.

The invention claimed is:

[1. A pump comprising:

a housing, a rotor path defined within the housing, an inlet formed in the housing at a first position on said rotor path, an outlet formed in the housing at a second position on said rotor path spaced from said first position, a rotor rotatable in said housing around an axis, the rotor having an outer surface which seals against said rotor path, and at least one chamber-forming concavity inwardly formed from said outer rotor surface, said concavity a) having a concave surface which is concave in planes including the rotor axis, b) being surrounded by said outer surface, and c) solely forming a conveying chamber travelling around said rotor path on rotation of the rotor to convey fluid around the housing; and a resilient seal carried by the housing, located on said rotor path and extending between the outlet and the inlet in the direction of rotation of said rotor, said resilient seal being adapted to seal with and be resiliently deformed by said outer surface surrounding said concavity to prevent fluid flow from said outlet to said inlet past the seal, and to seal with said concave surface of said concavity, as said concavity passes between the outlet and the inlet to squeeze fluid from the chamber into the outlet.]

[2. A pump according to claim 1, wherein the seal has a rotor-engaging surface having an axial and angular extent generally the same as the axial and angular extent of the at least one chamber-forming concavity of the rotor.]

[3. A pump according to claim 1, wherein the housing includes a generally cylindrical interior surface co-operating with the rotor to form said chamber.]

[4. A pump according to claim 3, wherein the seal interrupts said cylindrical interior surface, extending axially and circumferentially relative to said cylindrical interior surface.]

[5. A pump according to claim 4, wherein the seal projects radially inwardly of the cylinder defined by said cylindrical interior surface.]

[6. A pump according to claim 1, wherein the seal has angularly spaced first and second ends around the path of the rotor, the outlet being formed adjacent said first end.]

[7. A pump according to claim 6, wherein the housing includes a generally cylindrical interior surface forming said rotor path and co-operating with the rotor to form said chamber, the inlet and the outlet being formed in said cylindrical interior surface of the housing.]

[8. A pump according to claim 6, wherein the inlet and the outlet are formed in said seal.]

[9. A pump according to claim 1, wherein the seal has angularly spaced first and second ends around the path of the rotor, the inlet being formed adjacent said second end.]

[10. A pump according to claim 1, wherein the seal is formed by a block of resilient material.]

[11. A pump according to claim 1, wherein the seal is formed by a membrane and a member resiliently supporting the membrane, the membrane sealing against the rotor.]

[12. A pump according to claim 11, wherein the resilient member is formed by a container of fluid or gas under pressure.]

[13. A pump according to claim 11, wherein the resilient member is formed by a spring.]

[14. A pump according claim 1, wherein two or more chamber-forming concavities are provided on said rotor at axially aligned angularly spaced positions around the rotor, each chamber-forming concavity co-operating with said seal as the concave surface passes from said outlet to said inlet in the direction of rotation of the rotor.]

[15. A pump according claim 1, wherein the housing includes a second inlet and a second outlet spaced axially along the rotor from first-mentioned inlet and outlet, wherein the rotor includes at least one second chamber-forming concavity forming, with the housing, a second conveying chamber travelling around the housing between the second inlet and the second outlet to convey fluid from said second inlet to said second outlet, wherein the housing between the second outlet and the second inlet in the direction of rotation of the rotor includes a second resilient seal adapted to seal with and be resiliently deformed by the outer surface of said at least one second chamber-forming concavity to prevent fluid flow from said second outlet to said second inlet past said second seal, and to seal with a concave surface of said second concavity, as said second concavity passes between the second outlet and the second inlet to squeeze fluid from the second chamber into the second outlet.]

[16. A pump according to claim 15, wherein the rotor is:

movable axially in one direction to align the first-mentioned at least one chamber-forming concavity and the second inlet and second outlet while closing the first-mentioned inlet and the first-mentioned outlet, and moveable axially in an opposite direction to align the at least one chamber-forming concavity with the first inlet-mentioned and the first-mentioned outlet while closing the second inlet and the second outlet.]

[17. A pump according to claim 16, wherein the housing is formed of a resilient material, the rotor engaging and resiliently distending the housing to provide a fluid-tight seal between the housing and housing-contacting portions of the rotor.]

[18. A pump according to claim 17, wherein the housing has a generally cylindrical interior surface, wherein the rotor has a co-operating generally cylindrical exterior surface sealing against said interior surface, and wherein said at least one chamber-forming concavity is formed in said generally cylindrical exterior surface.]

[19. A pump according to claim 18, wherein said exterior surface is formed by a land on the rotor, the land having axially spaced ends and the rotor being provided with radially relieved portions at said ends.]

[20. A pump according to claim 18, wherein a circumferential rib is formed on each relieved portion, each rib sealing resiliently against the interior surface of said housing.]

[21. A pump according to claim 1, wherein only a single inlet and a single outlet are provided, the rotor conveying fluid from said inlet to said outlet.]

[22. A pump according to claim 1, further including a second inlet and a second outlet spaced circumferentially around the housing from the first mentioned inlet and outlet, the rotor further including a plurality of chamber-forming concavities conveying fluid from the first mentioned inlet to the first mentioned outlet and from the second inlet to the second outlet, and wherein the first mentioned seal is located between the second inlet and the first mentioned outlet and a second seal is provided between the first mentioned outlet and the second inlet.]

[23. A pump according to claim 22, wherein the rotor has at least four chamber-forming concavities.]

[24. A pump according to claim 1, wherein the rotation of the rotor is reversible to pump fluid from the outlet to the inlet.]

[25. A pump according to claim 1, further including a drive for rotating the rotor.]

[26. A pump according to claim 1, wherein the housing and seal are a unit including of an insert moulding, an over-moulding or a dual shot moulding.]

[27. A pump according to claim 1, wherein the housing, seal and rotor are a single injection moulding.]

[28. A pump comprising:

a housing, a rotor path defined within the housing, an inlet formed in the housing at a first position on said rotor path, an outlet formed in the housing at a second position on said rotor path spaced from said first position, a rotor rotatable in said housing, the rotor having at least two apices formed on the rotor and sealing against said rotor path, at least one first surface formed on said rotor between said at least two apices, and a chamber formed in said at least one first surface between the at least two apices and the housing, and travelling around said rotor path on rotation of the rotor to convey fluid around the housing, a resilient seal carried by the housing located on said rotor path and so extending between the outlet and the inlet in the direction of rotation of said rotor that each apex seals with, and resiliently deforms, the seal, as each apex passes between the outlet and the inlet to prevent fluid flow from said outlet to said inlet past the seal;

in which the rotor is movable axially relative to the housing between a first axial position and a second axial position, and the rotor further including at least one second chamber-forming surface spaced axially from said at least one first chamber-forming surface, the at least one first chamber-forming surface forming a chamber with the housing in said first axial position of the rotor and the at least one second chamber-forming surface forming a chamber with the housing in said second axial position of the rotor.]

[29. A pump according to claim 28, wherein the volume of the chamber formed by the at least one first chamber-forming surface is different from the volume of the chamber formed by the at least one second chamber-forming surface.]

[30. A pump according to claim 29, wherein the volume of the chamber formed by the at least one first chamber-forming surface is greater than the volume of the chamber formed by the at least one second chamber-forming surface.]

[31. A pump according to claim 28, wherein a device is provided for moving said rotor axially between said first and second axial positions.]

[32. A pump according to claim 31, in which rotation of said rotor in one direction acts to convey fluid from the inlet to the outlet with the rotor in the first axial position, in which rotation of said rotor in an opposite direction will move said rotor axially between said first and second axial positions, in which a reversal of rotation from the opposite direction to the one direction with the rotor in the second axial position will move the rotor back to the first axial position, and in which rotation in said opposite direction acts to convey fluid from the outlet to the inlet by said at least one second chamber-forming surface.]

[33. A pump according to claim 32, wherein said device includes a mechanism acting between the housing and the rotor for moving the rotor axially between the first and second axial positions relative to the housing depending on rotation of said rotor in the one or the opposite direction.]

[34. A pump according to claim 33, wherein said mechanism comprises a pin member and a helical slot member, one member being on the rotor and the other member being on the housing, rotation of the rotor between the one direction and the opposite direction moving the pin in a helical path along said slot to move the rotor axially between the first and second axial positions.]

[35. A pump comprising:

a housing, a rotor path defined within the housing, an inlet formed in the housing at a first position on said rotor path, an outlet formed in the housing at a second position on said rotor path spaced from said first position, a rotor rotatable in said housing, the rotor having at least two apices formed on the rotor and sealing against said rotor path, at least one surface formed on said rotor between said at least two apices, and a chamber formed by said at least one surface between the at least two apices and the housing, and travelling around said rotor path on rotation of the rotor to convey fluid around the housing, a resilient seal carried by the housing located on said rotor path and so extending between the outlet and the inlet in the direction of rotation of said rotor that each apex seals with, and resiliently deforms, the seal, as each apex passes between the outlet and the inlet to prevent fluid flow from said outlet to said inlet past the seal; and in which the rotor is movable axially relative to the housing between a first axial position in which the at least one chamber-forming surface forms a chamber with the housing and a second axial position in which the rotor cooperates with the housing to provide a direct communication between the inlet and the outlet.]

[36. A pump according to claim 35, wherein a device is provided for moving said rotor axially between said first and second axial positions.]

[37. A pump according to claim 36, in which rotation of said rotor in one direction acts to convey fluid from the inlet to the outlet with the rotor in the first axial position, in which rotation of said rotor in an opposite direction will move said rotor axially between said first and second axial positions, and in which a reversal of rotation from the opposite direction to the one direction with the rotor in the second axial position will move the rotor back to the first axial position.]

[38. A pump according to claim 37, wherein said device includes a mechanism acting between the housing and the rotor for moving the rotor axially between the first and second axial positions relative to the housing depending on rotation of said rotor in the one or the opposite direction.]

[39. A pump according to claim 38, wherein said mechanism comprises a pin member and a helical slot member, one member being on the rotor and the other member being on the housing, rotation of the rotor between the one direction and the opposite direction moving the pin in a helical path along said slot to move the rotor axially between the first and second axial positions.]

*40. A pump comprising:*

*a generally cylindrical housing formed of a resilient material,*

*a generally cylindrical rotor path defined within the housing,*

*an inlet formed in the housing at a first position on said rotor path,*

*an outlet formed in the housing at a second position on said rotor path spaced from said first position,*

*a generally cylindrical rotor rotatable in said housing around an axis, the rotor having*

*a cylindrical outer surface which seals against said rotor path, and*

*at least one chamber-forming concavity inwardly formed from said cylindrical outer rotor surface, said concavity*

*a) having a concave surface which is concave in planes including the rotor axis,*

*b) being surrounded by said outer surface, and*

*c) solely forming a conveying chamber travelling around said rotor path on rotation of the rotor to convey fluid around the housing;*

*a resilient seal formed by a membrane carried by the housing, located on said rotor path, and extending between a first axial edge of the housing adjacent to the inlet and a second axial edge of the housing adjacent to the outlet in the direction of rotation of said rotor, and*

*a resilient member that applies a resilient force to the membrane and resiliently supports the membrane, and*

*wherein said membrane is adapted to seal with and be resiliently deformed by said resilient member against said outer surface surrounding said concavity to prevent fluid flow from said outlet to said inlet past the membrane, and to seal with said concave surface of said concavity axially and circumferentially, as said concavity passes between the outlet and the inlet to squeeze fluid from the chamber into the outlet,*

*wherein the resilient material of the housing is capable of being deformed under load and distended by the rotor,*

*wherein the rotor is arranged to distend the housing,*

*wherein the housing and membrane are a unit made by an insert molding process, or an over molding process, or a dual shot molding process, or a single injection molding process, such that the fluid is prevented from passing between the membrane and the housing in use.*

*41. A pump according to claim 40, wherein the membrane has a rotor-engaging surface having an axial and angular extent generally the same as the axial and angular extent of the at least one chamber-forming concavity of the rotor.*

*42. A pump according to claim 40, wherein the housing includes a generally cylindrical interior surface co-operating with the rotor to form said chamber.*

*43. A pump according to claim 42, wherein the membrane interrupts said cylindrical interior surface, extending axially and circumferentially relative to said cylindrical interior surface.*

*44. A pump according to claim 43, wherein the membrane projects radially inwardly of the cylinder defined by said cylindrical interior surface.*

*45. A pump according to claim 40, wherein the membrane has angularly spaced first and second ends around the path of the rotor, the outlet being formed adjacent said first end.*

*46. A pump according to claim 45, wherein the housing includes a generally cylindrical interior surface forming said rotor path and co-operating with the rotor to form said chamber, the inlet and the outlet being formed in said cylindrical interior surface of the housing.*

*47. A pump according to claim 45, wherein the inlet and the outlet are partly formed in said membrane.*

*48. A pump according to claim 40, wherein the membrane has angularly spaced first and second ends around the path of the rotor, the inlet being formed adjacent said second end.*

*49. A pump according to claim 40, wherein the resilient member is formed by a container of fluid or gas under pressure.*

*50. A pump according to claim 40, wherein the resilient member is formed by a spring.*

*51. A pump according claim 40, wherein two or more chamber-forming concavities are provided on said rotor at axially aligned angularly spaced positions around the rotor, each chamber-forming concavity co-operating with said membrane as the concave surface passes from said outlet to said inlet in the direction of rotation of the rotor.*

*52. A pump according to claim 40, wherein the housing has a generally cylindrical interior surface,*

*wherein the rotor has a co-operating generally cylindrical exterior surface sealing against said interior surface;*

*wherein said at least one chamber-forming concavity is formed in said generally cylindrical exterior surface;*

*wherein said exterior surface is formed by a land on the rotor, the land having axially spaced ends and the rotor being provided with radially relieved portions at said ends; and*

*wherein a circumferential rib is formed on each relieved portion, each rib sealing resiliently against the interior surface of said housing.*

*53. A pump according to claim 40, wherein only a single inlet and a single outlet are provided, the rotor conveying fluid from said inlet to said outlet.*

*54. A pump according to claim 40, further including a second inlet and a second outlet spaced circumferentially around the housing from the first mentioned inlet and outlet, the rotor further including a plurality of chamber-forming concavities conveying fluid from the first mentioned inlet to the first mentioned outlet and from the second inlet to the second outlet, and wherein the first mentioned membrane is located between the second inlet and the first mentioned outlet and a second membrane is provided between the first mentioned outlet and the second inlet.*

*55. A pump according to claim 54, wherein the rotor has at least four chamber-forming concavities.*

*56. A pump according to claim 40, wherein the rotation of the rotor is reversible to pump fluid from the outlet to the inlet.*

*57. A pump according to claim 40, further including a drive for rotating the rotor.*

*58. A pump according to claim 40, wherein the housing and the membrane are a single injection molding.*

*59. A pump comprising:*

*a housing;*

*a rotor path defined within the housing;*

*a rotor rotatable in the housing around an axis;*

*an inlet formed in the housing at a first position on the rotor path;*

*an outlet formed in the housing at a second position on the rotor path;*

*a resilient seal formed by a membrane; and*

*a resilient member that applies a resilient force to the membrane and resiliently supports the membrane, and*

*wherein the housing is formed of resilient material capable of being deformed under load and distended by the rotor,*

*wherein the rotor has an outer surface that seals against the rotor path and a concavity inwardly formed from the outer rotor surface, the concavity being surrounded by the outer surface and forming a conveying chamber travelling around the rotor path on rotation of the rotor to convey fluid around the housing,*

*wherein the membrane is located on the rotor path and adapted to seal with and be resiliently deformed by the outer surface to prevent the fluid from flowing from the outlet to the inlet past the membrane, and to seal with the concavity as the concavity passes between the outlet and the inlet to squeeze the fluid from the chamber into the outlet,*

*wherein the housing and membrane are a unit made by an insert molding process, or an over molding process, or a dual shot molding process, or a single injection molding process, such that the fluid is prevented from passing between the membrane and the housing in use.*

* * * * *